(12) United States Patent
Kim et al.

(10) Patent No.: US 6,248,367 B1
(45) Date of Patent: Jun. 19, 2001

(54) BOVINE EXCRETION EXTRACTS HAVING ANTICANCER AND ANTI-INFLAMMATORY ACTIVITY AND PROCESS FOR PREPARING THE SAME

(75) Inventors: Bok Deuk Kim, 796-7, Mok-dong, Yangchun-ku, Seoul; Man Ki Park, Sungnam; Jeong Hill Park, Seoul; Seung Ki Lee, Seoul; Jin Ho Chung, Seoul; Sung Won Park, Seoul, all of (KR)

(73) Assignees: Bok Deuk Kim; Hun Wook Kim; Sung Yong Kim, all of Seoul (KR)

( * ) Notice: Subject to any disclaimer, the term of this patent is extended or adjusted under 35 U.S.C. 154(b) by 0 days.

(21) Appl. No.: 09/348,898

(22) Filed: Jul. 7, 1999

(30) Foreign Application Priority Data

Jul. 22, 1998 (KR) .............................................. 98-029460

(51) Int. Cl.⁷ .................................................. A61K 35/24
(52) U.S. Cl. ............................................................ 424/543
(58) Field of Search ............................................. 424/543

(56) References Cited

PUBLICATIONS

Hosono et al., Jpn J Zootech Sci 56(3): 274–278 (1985). Abstract.*
Chemical Abstracts, vol. 113, No. 11, p. 81, abstract 91505 (1990).
Database WPI on EPOQUE, week 9503, London: Derwent Publications Ltd., AN 95–019 182, PN: JP 06–305 970 A.
Database WPI on EPOQUE, week 8501, London: Derwent Publications Ltd., AN 85–004170, PN: JP 59–205 320 A.
Database WPI on EPOQUE, week 9716, London: Derwent Publications Ltd., AN 97–175677, PN: JP 09–040 657 A.

* cited by examiner

Primary Examiner—Jean C. Witz
(74) Attorney, Agent, or Firm—Dike, Bronstein, Roberts & Cushman; Peter F. Corless

(57) ABSTRACT

Disclosed are bovine excretion extracts having anticancer and anti-inflammatory activity prepared by a process comprising the step of extracting bovine excretion with a polar solvent selected from the group consisting of lower alcohol, lower ketone, acetonitrile, water and mixtures thereof, a process for preparing the same, and the use thereof as an anticancer agent or adjuvant, or an anti-inflammatory agent.

9 Claims, 2 Drawing Sheets

BOVINE EXCRETION EXTRACTS HAVING ANTICANCER AND ANTI-INFLAMMATORY ACTIVITY AND PROCESS FOR PREPARING THE SAME

TECHNICAL FIELD

The present invention relates to bovine excretion extracts and a process for preparing the same. More specifically, the present invention relates to bovine excretion extracts having not only anticancer activity by potent inhibition of cell proliferation and by anti-oxidation but also anti-inflammatory activity by potent inhibition of platelet aggregation, which are useful as an anticancer agent or adjuvant, or an anti-inflammatory agent, and the process for preparing the same.

BACKGROUND ART

The term "cancer" is a generic name of malignant tumors. It means the state wherein part of cells begin abnormal proliferation and continue the proliferation to invade neighboring normal tissues and to break down cell functions. Cells abnormally proliferate because they get out of the control of their regulatory mechanisms because they are genetically mutated.

Anticancer agents which have been developed hitherto for treating various cancers are broadly classified into chemical anticancer agents and immunological anticancer agents (modification substances of biological reactions). The chemical agents display their effect because proliferative potency of cancer cells is different from that of normal cells. The immunological agents expel cancer cells by reviving immunocompetence in an organism.

Chemical anticancer agents are usually toxic to the cells and display their effect based on the principle that cancer cells have stronger proliferative potency than normal cells. That is, if chemical anticancer agents which suppress cell proliferation are administered to a living body, cancer cells having stronger proliferative potency will be influenced more severely than normal cells.

Chemical anticancer agents which have been developed to the present time can be classified into five types: alkylating agents, metabolic antagonists, antibiotic anticancer agents, botanical anticancer agents, etc. Alkylating agents are medicines which display anticancer effect by alkylation of hydrogen atoms of nucleic acids or proteins. Metabolic antagonists are antagonists against purine or pyrimidine bases and display anticancer effect by inhibition of DNA replication. Antibiotic and botanical anticancer agents are derived from microorganisms and plants, respectively. Other examples of anticancer agents are L-asparaginase or cisplatin (platinum compound)

As described previously, chemical anticancer agents by inhibiting cell proliferation derived from microorganisms or plants have been already reported. However, anticancer agents derived from animals have not been reported in the art.

From old times, animal excretion has been used for treating various diseases in a folk remedy. That is, human excretion has been traditionally used for treating a cut or a bruise, and bovine excretion has been used for detoxification or treating a burn. In addition, it has been known that wounded animals take bovine excretion. As above-described, although animal excretion has been traditionally used for medicines, scientific studies thereon have not been performed to the present time. Moreover, it has not been expected that animal excretion can be used as an anticancer agent or adjuvant, or an anti-inflammatory agent.

DISCLOSURE OF THE INVENTION

Accordingly, the present inventors repeated scientific studies to find out physiological activity of bovine excretion. As a result, they discovered that bovine excretion extracts prepared by a process according to the present invention have anticancer activity by potent inhibition of cell proliferation and by anti-oxidation, and anti-inflammatory activity by potent inhibition of platelet aggregation, and finally, completed the present invention.

An object of the present invention is to provide novel bovine excretion extracts having anticancer activity by inhibition of cell proliferation and by anti-oxidation, and anti-inflammatory activity by inhibition of platelet aggregation, which are useful as an anticancer agent or adjuvant, or an anti-inflammatory agent.

Another object of the present invention is to provide a process for preparing the bovine excretion extracts.

The present invention provides bovine excretion extracts having anticancer and anti-inflammatory activity prepared by a process comprising the step of extracting bovine excretion with a polar organic solvent selected from the group consisting of lower alcohol having 1 to 4 carbon atom(s), lower ketone of the formula: $R_1COR_2$, wherein $R_1$ and $R_2$ independently of one another represent alkyl having 1 to 3 carbon atom(s), acetonitrile, water and mixtures thereof. In a preferable embodiment, the present bovine excretion extracts are prepared by re-extracting the extracts with a nonpolar organic solvent selected from the group consisting of water-saturated butanol, ethyl acetate and ethyl ether. And the bovine excretion is preferably excrement of cattle or buffaloes.

The present invention also provides an anticancer agent comprising the bovine excretion extracts as active ingredient. In a preferable embodiment, the anticancer agent is orally administered with a unit dose of 100 to 500 mg, about 3 times a day.

The present invention also provides an anti-inflammatory agent comprising the bovine excretion extracts as active ingredient. In a preferable embodiment, the anti-inflammatory agent is orally administered with a unit dose of 100 to 500 mg, about 3 times a day.

The present invention provides a process for preparing bovine excretion extracts having anticancer and anti-inflammatory activity comprising the step of extracting bovine excretion with a polar solvent selected from the group consisting of lower alcohol having 1 to 4 carbon atom(s), lower ketone of the formula: $R_1COR_2$, wherein $R_1$ and $R_2$ independently of one another represent alkyl having 1 to 3 carbon atom(s), acetonitrile, water and mixtures thereof. In a preferable embodiment, the process further comprises the step of re-extracting the extracts with a nonpolar organic solvent selected from the group consisting of water-saturated butanol, ethyl acetate and ethyl ether.

BEST MODE FOR CARRYING OUT THE INVENTION

Figure 1A:
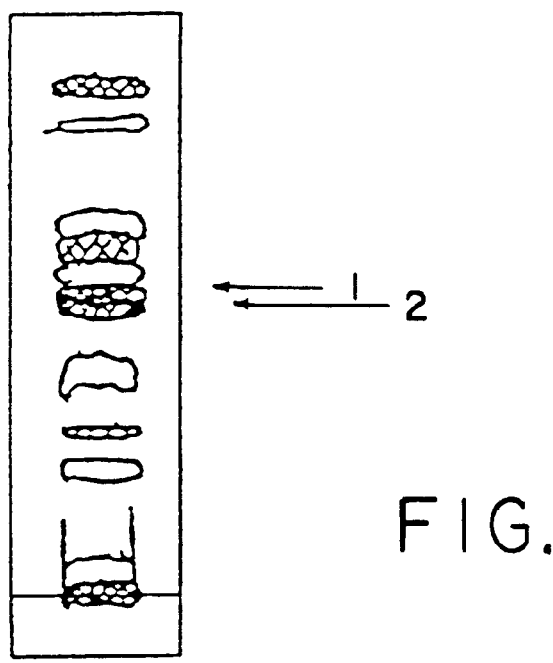
FIG. 1a shows a result of thin layer chromatography on silica gel of the bovine excretion extracts prepared in example 1.

Hereinafter, the present invention will be more specifically explained. In the present invention, the term "bovine excretion" means "excretion from animals of family Bovidae". Family Bovidae includes all the animals belonging to family Bovidae in accordance with zoological taxonomy. In particular, cattle or buffaloes are preferable in the present invention.

Bovine excretion extracts according to the present invention are prepared by collecting fresh bovine excretion and then extracting the excretion with a polar solvent such as lower alcohol, lower ketone, acetonitrile, water or mixtures thereof. The lower alcohol is one having 1 to 4 carbon atom(s) and particularly, methanol or ethanol. The lower ketone is one having the formula: $R_1COR_2$, wherein $R_1$ and $R_2$ independently of one another represent alkyl having 1 to 3 carbon atom(s), and particularly, acetone or methyl ethyl ketone.

The bovine excretion extracts of the present invention may be prepared as above and more preferably, may be prepared by subsequently suspending the extracts in water followed by re-extracting the suspended extracts with a nonpolar organic solvent such as water-saturated butanol, ethyl acetate or ethyl ether.

Various ingredients derived from fodder which has been taken by cattle may be comprised in the bovine excretion extracts. These are ingredients as such which are comprised in fodder or modified ingredients thereof. The modified ingredients are produced by metabolism of original ingredients by the actions of digestive fluid, digestive enzymes or enteric bacteria in the gastrointestinal tract. The extracts may also comprise various digestive fluid secreted from the bovine digestive tract.

The bovine excretion extracts of the present invention have anticancer activity by inhibition of cell proliferation and by anti-oxidation and an anti-inflammatory activity by inhibition of platelet aggregation and therefore, may be useful as an anticancer agent or adjuvant, or an anti-inflammatory agent. That is, an anticancer agent or adjuvant, or an anti-inflammatory agent may comprise the bovine excretion extracts of the present invention as active ingredient. The agent is preferably orally administered in the present invention. Hence, the extracts may be pharmaceutically manufactured into orally administrable dosage forms such as conventional tablets, hard or soft capsules, solution or suspension in combination with pharmaceutically acceptable carriers. The pharmaceutically acceptable carriers are binders, lubricants, disintegrators, excipients, solubilizers, stabilizers, suspending agents, colorants or flavoring agents. The anticancer or anti-inflammatory agent of the present invention may be preferably administered with a unit dose of 100~500 mg, three times a day. In the above case, effective anticancer or anti-inflammatory activity can be expected.

EXAMPLES

This invention will be better understood from the following examples. However, one skilled in the art will readily appreciate the specific examples described are merely illustrative of, and are not intended to, nor should be intended to, limit the invention as described more fully in the claims which follow thereafter.

Example 1
Preparation of Bovine Excretion Extracts 10 l of methanol was added to 10 kg of fresh bovine excretion and the mixture was refluxed under heating to a temperature of 60° C. for 1 hour. The extracts prepared thereby were filtered and organic solvent was removed from the filtrate under reduced pressure. Subsequently, the extracts were further extracted with water-saturated butanol to obtain 2.5 g of nonpolar fraction. The fraction was filtered and dried to obtain the extracts as powder. The extracts prepared thereby were analyzed using thin layer chromatography on silica gel with mobile phase of chloroform and methanol in a ratio of 50 to 1. The result is shown in FIG. 1a. In FIG. 1a, dot ① indicates stigmastanol ($C_{29}H_{52}O$) and dot ② indicates beta-cytosterol ($C_{29}H_{50}O$), respectively.

Figure 1B:
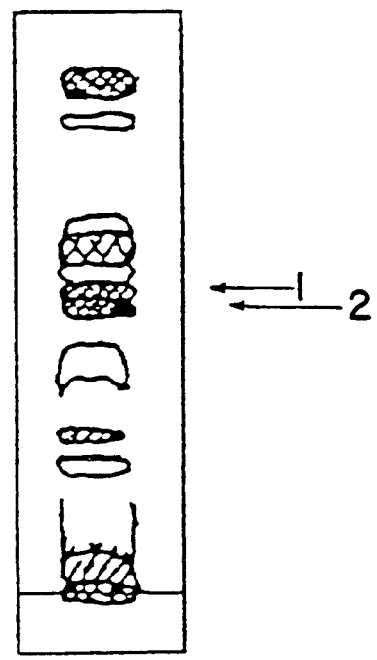
FIG. 1b shows a result of thin layer chromatography on silica gel of the bovine excretion extracts prepared in example 2.

Example 2
Preparation of Bovine Excretion Extracts 10 l of anhydrous ethanol was added to 10 kg of fresh bovine excretion and the mixture was intimately stirred for 2 hours and then, allowed to stand. The extracts prepared thereby were filtered to remove debris and precipitates. The filtrate prepared thereby was concentrated under reduced pressure and dried to obtain 3.0 g of low molecular-weight fraction as powder. The extracts prepared thereby were analyzed using thin layer chromatography on silica gel with mobile phase of chloroform and methanol in a ratio of 50 to 1. The result is shown in FIG. 1b. In FIG. 1b, dot ① indicates stigmastanol ($C_{29}H_{52}O$) and dot ② indicates beta-cytosterol ($C_{29}H_{50}O$), respectively.

Test Example 1
Cytotoxicity Test

Cytotoxicity of the bovine excretion extracts according to the present invention was tested by measuring degree of hemolysis of erythrocytes. To erytlirocytes isolated from rats, the extracts prepared in example 1 were added and then, the mixture was cultivated at a temperature of 37° C. for 30, 60 and 120 minutes, respectively. After centrifugation, 400 µl of medium was taken and then reagent for detection of hemolysis was added thereto. Then, absorbance was read at 540 nm to determine degree of hemolysis. Degree of hemolysis (%) is calculated as follows:

$$\text{Degree of hemolysis } (\%) = \frac{\text{absorbance of the supernatent}}{\text{absorbance of erythrocytes which have } 100\% \text{ of degree of hemolysis}} \times 100$$

Erythrocytes treated with menadione (positive control) were measured on degree of hemolysis, for the purpose of comparison with the bovine excretion extracts prepared in example 1. Menadione is a known compound which induce hemolysis of erythrocytes. The result of measuring cytotoxicity by degree of hemolysis is shown in the following table 1.

TABLE 1

| Cytotoxic effect of extracts of example 1 on erythrocytes | | | | |
|---|---|---|---|---|
| time (min) | 0 | 30 | 60 | 120 |
| group treated with the extracts of example 1 | 0.0 | 2.3 ± 0.2 | 2.1 ± 0.5 | 2.6 ± 1.9 |
| control group | 0.0 | 0.3 | 1.7 | 1.5 |
| menadione-treated group | 0.0 | 1.6 ± 1.3 | 2.3 ± 0.4 | 65.3 ± 4.8 |

As shown in the above table 1, in the case of menadione-treated group, cytotoxicity was significantly increased as determined by hemolysis of erythrocytes. However, in the case of being treated with the extracts of example 1, hemolysis of erythrocytes was not occurred even at a high concentration, i.e. 50 µg/ml of the extracts and did not exhibit any significant difference with control group. Therefore, these data suggest that the bovine excretion extracts according to the present invention was not toxic to the cells.

Test Example 2
Anticancer Activity Test by Measuring Thymidine Uptake Amount

Anticancer activity of the extracts prepared in examples 1 and 2 was tested by measuring thymidine uptake amount as described in the following. 13.8 g of DMEM (Dulbecco's Modified Eagle's Medium, Gibco) was dissolved in 1 l of deionized water and the solution was adjusted to a pH of 7.4 with sodium carbonate and hydrochloric acid solutions. Then, 10% of calf serum, $1 \times 10^{-7}$ M of insulin and 50 mg/l of gentamycin were added thereto and the whole was sterilized by millipore filter to prepare cultivation medium. To that medium, human hepatoma cells sk-Hep-1 obtained from Cancer Research Center of Seoul National University in the Republic of Korea were inoculated, the number of which was $1 \times 10^6$ per 25 cm$^2$ of T flask and then incubated for 48 hours under 5% of $CO_2$ gas at a temperature of 37° C.

The cultivate was transferred to 24-well cultivation container and was successively cultured for one day and then, the bovine extracts prepared in examples 1 and 2 were respectively added thereto up to a concentration of 1~200 µg/ml. 12 hours after addition, $^3$H-labelled thymidine was added up to a concentration of 1 µCi/ml. Further, 12 hours after addition, medium was removed from each well and cells were fixed with methanol, washed with PBS (phosphate buffered saline), and then, washed twice with 10% of trichloroacetic acid to remove residual radioactive thymidine. The cells were dissolved with 1 M of sodium hydroxide and the solution was neutralized with 1 M of hydrochloric acid. The radioactivity incorporated into DNA was measured using scintillation counter (Pharmacia 1024).

Figure 2A:
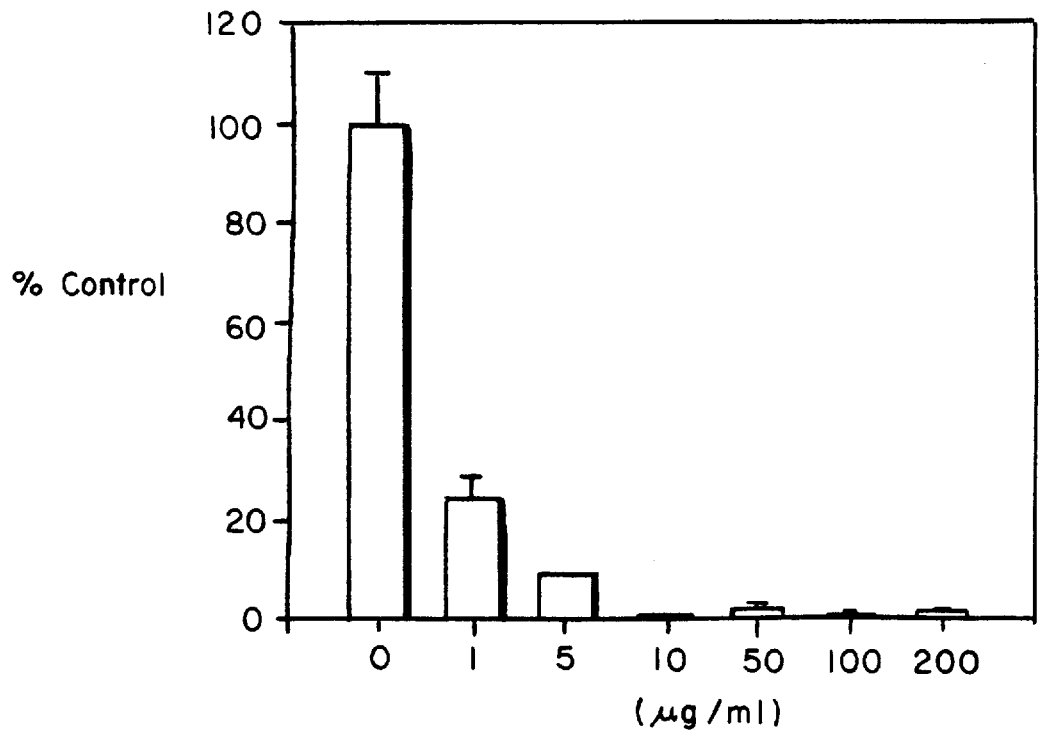
FIG. 2a is a graph which shows a result of screening anticancer activity of the bovine excretion extracts prepared in example 1.
Figure 2B:
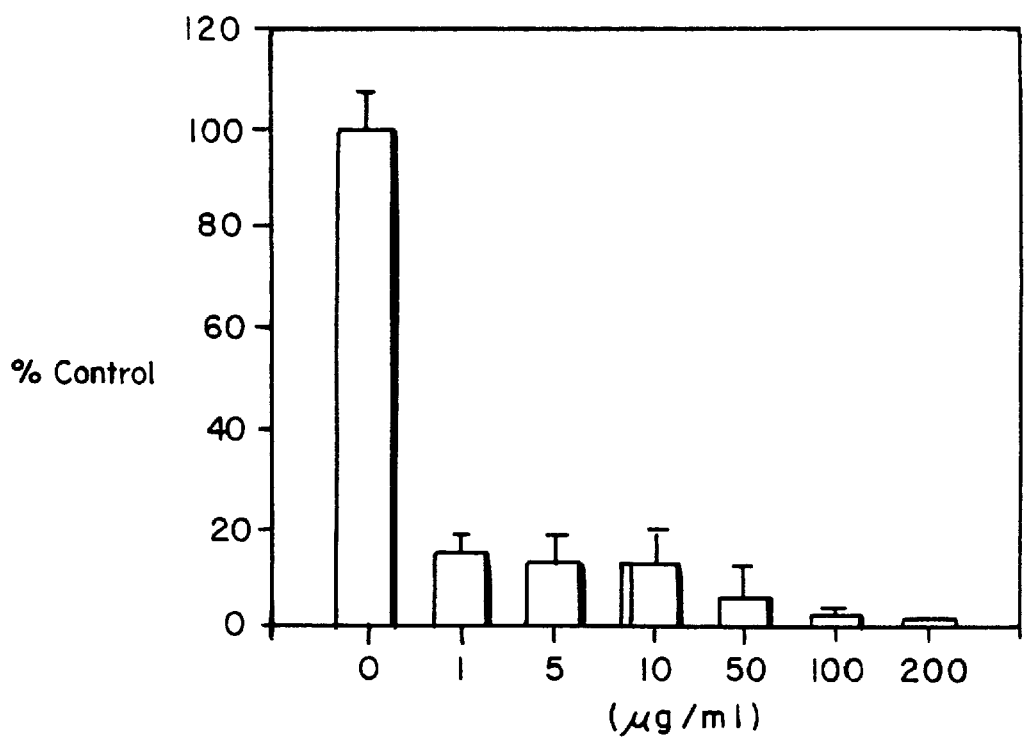
FIG. 2b is a graph which shows a result of screening anticancer activity of the bovine excretion extracts prepared in example 2.

The result is shown in FIGS. 2a and 2b, respectively. FIGS. 2a and 2b are graphs which show results of the bovine excretion extracts of examples 1 and 2, respectively. In the above figures, a concentration of sample is plotted on the axis of abscissa and a thymidine uptake amount is plotted on the axis of ordinates.

As shown in the above figures, the bovine excretion extracts of examples 1 and 2 significantly decrease a thymidine uptake amount at a concentration of more than 1 µg/ml, which suggests that they inhibit proliferation of cancer cells sk-Hep-1. Therefore, the bovine excretion extracts according to the present invention significantly inhibit proliferation of cancer cells and hence, are expected to be very useful as an anticancer agent or adjunctive.

Test Example 3
Anti-inflammatory Activity Test by Measuring Inhibition of Platelet Aggregation Anti-inflammatory activity of the extracts prepared in example 1 was tested by measuring inhibition of platelet aggregation as described in the following. Platelet rich plasma (PRP) were obtained from rat blood and the number of platelets was adjusted to $3 \times 10^8$/ml. 489 µl of PRP was each placed in a glass container for measuring platelet aggregation and was pre-incubated for 1 minute at 37° C. 2.5 µl of a solution of the extracts prepared in example 1 dissolved in methanol was added thereto and 3 minutes after addition, 8 µl of thrombin solution was added. Then, the inhibitory effect on platelet aggregation was measured using a platelet-aggregometer. The result is shown in table 2.

TABLE 2

| Anti-inflammatory activity by inhibition of platelet aggregation | | | |
| --- | --- | --- | --- |
| Extracts of example 1 (µg/ml) | 1.25 | 2.5 | 5.0 |
| Inhibition of platelet aggregation (%) | 42.6 | 57.4 | 54.3 |

As shown in table 2, the extracts of example 1 significantly inhibit platelet aggregation. Therefore, the extracts of the present invention are expected to be very useful as an anti-inflammatory agent.

Accordingly, the bovine excretion extracts of the present invention are expected to be very useful as an anticancer agent or adjuvant by inhibition of cell proliferation and by anti-oxidation or an anti-inflammatory agent by inhibition of platelet aggregation.

What is claimed is:

1. Bovine excretion extracts having anticancer and anti-inflammatory activity prepared by a process comprising extracting bovine excretion with a polar solvent selected from the group consisting of lower alcohol having 1 to 4 carbon atom(s), lower ketone of the formula: $R_1COR_2$, wherein $R_1$ and $R_2$ independently of one another represent alkyl having 1 to 3 carbon atom(s), acetonitrile, water and mixtures thereof; and retracting said extracts with a nonpolar organic solvent selected from the group consisting of water-saturated butanol, ethyl acetate and ethyl ether.

2. The bovine excretion extracts according to claim 1 wherein the bovine excretion is excrement of cattle or buffaloes.

3. An anticancer agent comprising a bovine excretion extract of claim 1 or 2.

4. The anticancer agent according to claim 3 which is orally administered with a unit dose of 100 to 500 mg, about 3 times a day.

5. An anti-inflammatory agent comprising a bovine excretion extract of claim 1 or 2.

6. The anti-inflammatory agent according to claim 6 which is orally administered with a unit dose of 100 to 500 mg, about 3 times a day.

7. A process for preparing bovine excretion extracts having anticancer and anti-inflammatory activity prepared by a process comprising:

extracting bovine excretion with a polar solvent selected from the group consisting of lower alcohol having 1 to 4 carbon atom(s), lower ketone of the formula: $R_1COR_2$, wherein $R_1$ and $R_2$ independently of one another represent alkyl having 1 to 3 carbon atom(s), acetonitrile, water and mixtures thereof; and re-extracting said extracts with a nonpolar organic solvent selected from the group consisting of water-saturated butanol, ethyl acetate and ethyl ether.

8. An pharmaceutical composition formulated in a unit oral dosage of 100 to 500 mg and comprising a bovine excretion extract obtained by a process comprising extracting bovine excretion with a polar solvent selected from the group consisting of lower alcohol having 1 to 4 carbon atom(s), lower ketone of the formula: $R_1COR_2$, wherein $R_1$ and $R_2$ independently of one another represent alkyl having 1 to 3 carbon atom(s), acetonitrile, water and mixtures thereof.

9. The pharmaceutical composition of claim 8 further comprising a pharmaceutically acceptable carrier.

* * * * *